United States Patent [19]

Cohen et al.

[11] Patent Number: 5,675,014
[45] Date of Patent: Oct. 7, 1997

[54] PROCESS FOR THE PREPARATION OF ORGANOSILICON DISULFIDE COMPOUNDS

[75] Inventors: Martin Paul Cohen, Fairlawn; Dane Kenton Parker, Massillon; Lawson Gibson Wideman, Tallmadge, all of Ohio

[73] Assignee: The Goodyear Tire & Rubber Company, Akron, Ohio

[21] Appl. No.: 589,279

[22] Filed: Jan. 22, 1996

[51] Int. Cl.⁶ ............... C07D 277/60; C07F 7/02; C07F 7/08
[52] U.S. Cl. ............... 548/110; 556/469; 556/478; 556/482; 556/487; 556/489
[58] Field of Search ............... 548/110; 556/469, 556/478, 482, 487, 489

[56] References Cited

U.S. PATENT DOCUMENTS

| | | | |
|---|---|---|---|
| 3,768,537 | 10/1973 | Hess et al. | 152/330 |
| 3,842,111 | 10/1974 | Meyer-Simon | 260/448.2 |
| 4,390,648 | 6/1983 | Stacy | 523/216 |
| 4,820,751 | 4/1989 | Takeshita et al. | 523/215 |
| 5,440,064 | 8/1995 | Agostini et al. | 556/427 |

FOREIGN PATENT DOCUMENTS

| | | | |
|---|---|---|---|
| 0676443 | 3/1995 | European Pat. Off. | C08K 3/36 |
| 124400 | 6/1984 | Japan | C08L 21/00 |

OTHER PUBLICATIONS

Brzezinska, E, and Ternay, Andrew L, *J. Org. Chem.* 1994, 59, 8239–8244. "Disulfides. 1. Synthesis Using 2,2'", –Dithiobis(benzothiazole).

The Abstract for JP 7228588–A relates to sulfur–containing organosilicon compounds which are prepared by reacting sodium sulfite with sulfur to give sodium polysulfide followed by an in situ reaction with a haloalkoxysilane. (Aug. 29, 1995).

*Primary Examiner*—Johann Richter
*Assistant Examiner*—Jane C. Osiecki
*Attorney, Agent, or Firm*—Bruce J. Hendricks

[57] ABSTRACT

The present invention relates to a process for the preparation of organo silicon disulfide compounds. The process involves reacting a mercaptoalkoxysilane with a dithiobis (benzothiazole) compound.

11 Claims, No Drawings

PROCESS FOR THE PREPARATION OF ORGANOSILICON DISULFIDE COMPOUNDS

BACKGROUND OF THE INVENTION

The present invention relates to a process for the preparation of organosilicon disulfide compounds. Organosilicon disulfides are known adhesion promoters in sulfur-vulcanizable rubber mixtures reinforced with inorganic materials such as glass $SiO_2$, aluminosilicates and carbon black. For example, in GB 1,484,909, there is disclosed a process for the preparation of organo trialkoxysilane disulfides. In accordance with the teachings of this reference, mercaptopropyl trimethoxy silane or mercaptopropyl triethoxy silane is reacted with sulfuryl chloride in an inert solvent at temperatures of from 0° to 100°. The disulfide is then obtained by fractional distillation. The yields of desired product range in the neighborhood of 63 to 65 percent of theoretical.

U.S. Pat. No. 3,842,111 discloses a method for the preparation of organosilicon disulfide compounds by oxidizing mercaptoalkoxysilanes. Representative oxidizing agents include oxygen, chlorine, halogens of atomic weight 35 to 127, nitric oxide, sulfuryl chloride and sulfoxides.

Generally speaking, organosilicon disulfide compounds are very expensive and, with the increasing interest in silica-reinforced vulcanizable rubber, more cost-efficient methods of preparing these compounds are needed.

SUMMARY OF THE INVENTION

The present invention relates to a process for the preparation of organosilicon disulfide compounds. The present invention may be used to prepare symmetrical organosilicon disulfide compounds of the formula:

$$Z-R^1-S_2-R^1-Z,\qquad I$$

unsymmetrical organosilicon disulfide compounds of the formula

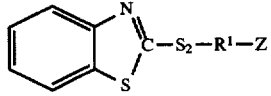

and mixtures thereof wherein Z is selected from the group consisting of

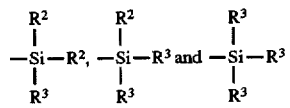

wherein $R^2$ may be the same or different and is independently selected from the group consisting of an alkyl group having 1 to 4 carbons and phenyl; $R^3$ may be the same or different and is independently selected from the group consisting of alkoxy groups having 1 to 8 carbon atoms and cycloalkoxy groups with 5 to 8 carbon atoms; and $R^1$ is selected from the group consisting of a substituted or unsubstituted alkylene group having a total of 1 to 18 carbon atoms and a substituted or unsubstituted arylene group having a total of 6 to 12 carbon atoms.

DETAILED DESCRIPTION OF THE INVENTION

There is disclosed a process for the preparation of organosilicon disulfide compounds comprising reacting (a) the dithiobis(benzothiazole) compound of the formula

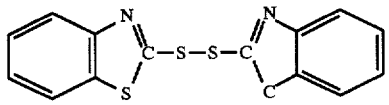

with (b) mercaptosilane compound of the formula

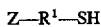

$$Z-R^1-SH\qquad IV$$

wherein Z is selected from the group consisting of

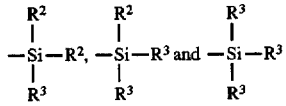

wherein $R^2$ may be the same or different and is independently selected from the group consisting of an alkyl group having 1 to 4 carbons and phenyl; $R^3$ may be the same or different and is independently selected from the group consisting of alkoxy groups having 1 to carbon atoms and cycloalkoxy groups with 5 to 8 carbon atoms; and $R^1$ is selected from the group consisting of a substituted or unsubstituted alkylene group having a total of 1 to 18 carbon atoms and a substituted or unsubstituted arylene group having a total of 6 to 12 carbon atoms.

The present invention relates to a process for the preparation of organosilicon disulfide compounds. Representative organosilicon disulfide compounds of formula I which may be prepared in accordance with the present invention include 2,2'-bis(trimethoxysilylethyl)disulfide; 3,3'-bis (trimethoxysilylpropyl)disulfide; 3,3'-bis (triethoxysilylpropyl)disulfide; 2,2'-bis (triethoxysilylpropyl)disulfide; 2,2'-bis (tripropoxysilylethyl)disulfide; 2,2'-bis(tri-sec-butoxysilylethyl)disulfide; 3,3'-bis(tri-t-butoxysilylethyl) disulfide; 3,3'-bis(triisopropoxysilylpropyl)disulfide; 3,3'-bis(trioctoxysilylpropyl)disulfide; 2,2'-bis(2'-ethylhexoxysilylethyl)disulfide; 2,2'-bis(dimethoxy ethoxysilylethyl)disulfide; 3,3'-bis (methoxyethoxypropoxysilylpropyl)disulfide; 3,3'-bis (dimethoxymethylsilylpropyl)disulfide; 3,3'-bis(methoxy dimethylsilylpropyl)disulfide; 3,3'-bis (diethoxymethylsilylpropyl)disulfide, 3,3'-bis(ethoxy dimethylsilylpropyl)disulfide, 3,3'-bis(cyclohexoxy dimethylsilylpropyl)disulfide; 4,4'-bis(trimethoxysilylbutyl) disulfide; 3,3'-bis(trimethoxysilyl-3-methylpropyl)disulfide; 3,3'-bis(tripropoxysilyl-3-methylpropyl)disulfide; 3,3'-bis (dimethoxy methylsilyl-3-ethylpropyl)disulfide; 3,3'-bis (trimethoxysilyl-2-methylpropyl)disulfide; 3,3'-bis (dimethoxyphenylsilyl-2-methylpropyl)disulfide; 3,3'-bis (trimethoxysilylcyclohexyl)disulfide; 12,12'-bis (trimethoxysilyldodecyl)disulfide; 12,12'-bis (triethoxysilyldodecyl)disulfide; 18,18'-bis (trimethoxysilyloctadecyl)disulfide; 18,18'-bis (methoxydimethylsilyloctadecyl)disulfide; 2,2'-bis (trimethoxysilyl-2-methylethyl)disulfide; 2,2'-bis (tripropoxysilyl-2-methylethyl)disulfide; 2,2'-bis (trioctoxysilyl-2-methylethyl)disulfide; 2,2'-bis (trimethoxysilyl-phenyl)disulfide; 2,2'-bis(triethoxysilyl-phenyl)disulfide; 2,2'-bis(trimethoxysilyl-tolyl)disulfide; 2,2'-bis(triethoxysilyl-tolyl)disulfide; 2,2'-bis (trimethoxysilyl-methyl tolyl)disulfide; 2,2'-bis (triethoxysilyl-methyl tolyl)disulfide; 2,2'-bis (trimethoxysilyl-ethyl phenyl)disulfide; 2,2'-bis (triethoxysilyl-ethyl phenyl)disulfide; 2,2'-bis (trimethoxysilyl-ethyl tolyl)disulfide; 2,2'-bis(triethoxysilyl-ethyl tolyl)disulfide; 3,3'-bis(trimethoxysilyl-propyl phenyl) disulfide; 3,3'-bis(triethoxysilyl-propyl phenyl)disulfide; 3,3'-bis(trimethoxysilyl-propyl tolyl)disulfide; and 3,3'-bis (triethoxysilyl-propyl tolyl)disulfide.

With reference to formula I, preferably $R^1$ is a alkylene group having 2 to 3 carbon atoms.

Z is

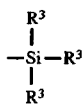

and $R^3$ is an alkoxy group having from 1 to 3 carbon atoms.

Representative organosilicon disulfide compounds of formula II which may be prepared in accordance with the present invention include 2-benzothiazyl-(3-triethoxysilylpropyl)disulfide; 2-benzothiazyl-(2-trimethoxysilylethyl)disulfide; 2-benzothiazyl-(3-trimethoxysilylpropyl)disulfide; 2-benzothiazyl-(2-triethoxysilylpropyl)disulfide; 2-benzothiazyl-(3-triethoxysilylpropyl)disulfide; 2-benzothiazyl-(2-tripropoxysilylethyl)disulfide; 2-benzothiazyl-(2-tri-sec-butoxysilylethyl)disulfide; 2-benzothiazyl-(3-tri-t-butoxysilylethyl)disulfide; 2-benzothiazyl-(3-triisopropoxysilylpropyl)disulfide; 2-benzothiazyl-(3-trioctoxysilylpropyl)disulfide; 2-benzothiazyl-(2-2'-ethylhexoxysilylethyl)disulfide; 2-benzothiazyl-(2-dimethoxy ethoxysilylethyl)disulfide; 2-benzothiazyl-(3-methoxyethoxypropoxysilylpropyl)disulfide; 2-benzothiazyl-(3-dimethoxymethylsilylpropyl)disulfide; 2-benzothiazyl-(3-methoxy dimethylsilylpropyl)disulfide; 2-benzothiazyl-(3-diethoxymethylsilylpropyl)disulfide; 2-benzothiazyl-(3-ethoxydimethylsilylpropyl)disulfide; 2-benzothiazyl-(3-cyclohexoxy dimethylsilylpropyl) disulfide; 2-benzothiazyl-(4-trimethoxysilylbutyl)disulfide; 2-benzothiazyl-(3-trimethoxysilyl-3-methylpropyl) disulfide; 2-benzothiazyl-(3-tripropoxysilyl-3-methylpropyl)disulfide; 2-benzothiazyl-(3-dimethoxy methylsilyl-3-ethylpropyl)disulfide; 2-benzothiazyl-(3-trimethoxysilyl-2-methylpropyl)disulfide; 2-benzothiazyl-(3-dimethoxyphenylsilyl-2-methylpropyl)disulfide; 2-benzothiazyl-(3-trimethoxysilylcyclohexyl)disulfide; 2-benzothiazyl-(12-trimethoxysilyldodecyl)disulfide; 2-benzothiazyl-(12-triethoxysilyldodecyl)disulfide; 2-benzothiazyl-(18-trimethoxysilyloctadecyl)disulfide; 2-benzothiazyl-(18-methoxydimethylsilyloctadecyl) disulfide; 2-benzothiazyl-(2-trimethoxysilyl-2-methylethyl) disulfide; 2-benzothiazyl-(2-tripropoxysilyl-2-methylethyl) disulfide; 2-benzothiazyl-(2-trioctoxysilyl-2-methylethyl) disulfide; 2-benzothiazyl-(2-trimethoxysilyl-phenyl) disulfide; 2-benzothiazyl-(2-triethoxysilyl-phenyl)disulfide; 2-benzothiazyl-(2-trimethoxysilyltolyl)disulfide; 2-benzothiazyl-(2-triethoxysilyltolyl)disulfide; 2-benzothiazyl-(2-trimethoxysilylmethyl tolyl)disulfide; 2-benzothiazyl-(2-triethoxysilyl-methyl tolyl)disulfide; 2-benzothiazyl-(2-trimethoxysilyl-ethyl phenyl)disulfide; 2-benzothiazyl-(2-triethoxysilyl-ethyl phenyl)disulfide; 2-benzothiazyl-(2-trimethoxysilylethyl tolyl)disulfide; 2-benzothiazyl-(2-triethoxysilyl-ethyl tolyl)disulfide; 2-benzothiazyl-(3-trimethoxysilyl-propyl phenyl)disulfide; 2-benzothiazyl-(3-triethoxysilyl-propyl phenyl)disulfide; 2-benzothiazyl-(3-trimethoxysilyl-propyl tolyl)disulfide; and 2-benzothiazyl-(3-triethoxysilyl-propyl tolyl)disulfide.

The desired products are prepared by reacting the dithiobis(benzothiazole) compound of formula III with a mercaptosilane compound of formula IV. Representative examples of compounds of formula IV include 2-mercaptoethyl trimethoxysilane, 3-mercaptopropyl trimethoxysilane, 3-mercaptopropyl triethoxysilane, 2-mercaptopropyl triethoxysilane, 2-mercaptoethyl tripropoxysilane, 2-mercaptoethyl tri sec-butoxysilane, 3-mercaptopropyl tri-t-butoxysilane, 3-mercaptopropyl tri-isopropoxysilane; 3-mercaptopropyl trioctoxysilane, 2-mercaptoethyl tri-2'-ethylhexoxysilane, 2-mercaptoethyl dimethoxy ethoxysilane, 3-mercaptopropyl methoxyethoxypropoxysilane, 3-mercaptopropyl dimethoxy methylsilane, 3-mercaptopropyl methoxy dimethylsilane, 3-mercaptopropyl ethoxy dimethylsilane, 3-mercaptopropyl diethoxy methylsilane, 3-mercaptopropyl cyclohexoxy dimethyl silane, 4-mercaptobutyl trimethoxysilane, 3-mercapto-3-methylpropyltrimethoxysilane, 3-mercapto-3-methylpropyl-tripropoxysilane, 3-mercapto-3-ethylpropyl-dimethoxy methylsilane, 3-mercapto-2-methylpropyl trimethoxysilane, 3-mercapto-2-methylpropyl dimethoxy phenylsilane, 3-mercaptocyclohexyl-trimethoxysilane, 12-mercaptododecyl trimethoxy silane, 12-mercaptododecyl triethoxy silane, 18-mercaptooctadecyl trimethoxysilane, 18-mercaptooctadecyl methoxydimethylsilane, 2-mercapto-2-methylethyltripropoxysilane, 2-mercapto-2-methylethyltrioctoxysilane, 2-mercaptophenyl trimethoxysilane, 2-mercaptophenyl triethoxysilane; 2-mercaptotolyl trimethoxysilane; 2-mercaptotolyl triethoxysilane; 1-mercaptomethyltolyl trimethoxysilane; 1-mercaptomethyltolyl triethoxysilane; 2-mercaptoethylphenyl trimenhoxysilane; 2-mercaptoethylphenyl triethoxysilane; 2-mercaptoethyltolyl trimethoxysilane; 2-mercaptoethyltolyl triethoxysilane; 3-mercaptopropylphenyl trimethoxysilane; 3-mercaptopropylphenyl triethoxysilane; 3-mercaptopropyltolyl trimethoxysilane; and 3-mercaptopropyltolyl triethoxysilane.

With reference to formula IV, preferably Z is

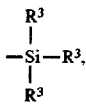

$R^3$ is an alkoxy group having from 1 to 3 carbon atoms and $R^1$ is an alkylene group having 2 to 3 carbon atoms.

The molar ratio of the compound of formula III to the compound of formula IV may range from 1:5 to 5:1. Preferably, the molar ratio ranges from 1:3 to 3:1 with a range of from 1:1 to 1:2 being particularly preferred.

The reaction should be conducted in the absence of water because the presence of an alkoxysilane moiety may be hydrolysed by contact with water.

The reaction of the present invention may be conducted in the presence of an organic solvent. Suitable solvents which may be used include chloroform, dichloromethane, carbon tetrachloride, hexane, heptane, cyclohexane, xylene, benzene, dichloroethylene, trichloroethylene, dioxane, diisopropyl ether, tetrahydrofuran and toluene. As indicated above, care should be exercised to avoid the presence of water during the reaction. Therefore, none of the above solvent should contain any appreciable levels of water. Preferably, the organic solvent is chloroform, heptane, cyclohexane, xylene and toluene.

The reaction may be conducted over a variety of temperatures. Generally speaking, the reaction is conducted in a temperature ranging from 20° C. to 140° C. Preferably, the reaction is conducted at a temperature ranging from 50° C. to 90° C.

The process of the present invention may be conducted at a variety of pressures. Generally speaking, however, the reaction is conducted at a pressure ranging from 0.096 to 4.83 kg/cm².

EXAMPLE 1

Preparation of 2-Benzothiazlyl-(3-Triethoxysilyl) Propyl Disulfide and Bis(3-Triethoxysilyl)Propyl Disulfide A 2-quart (1.89 liter) glass reactor was charged with 1400 ml of mixed xylenes, 142.8 g (0.60 mole) of 3-mercaptopropyltriethoxysilane, 216 g (0.60 mole) of 92 percent pure 2,2'-dibenzothiazyl disulfide with stirring. Within a few minutes, a mild exotherm to about 30° C. was noted and a clear amber solution formed. The reaction was stirred for 12 hours and a thick precipitate of mercaptobenzothiazole had formed and was removed by filtration. The xylenes were stripped under 29 inches of Hg vacuum, wherein the liquid product mixture was decanted from additional mercaptobenzothiazole. The combined dried mercaptobenzothiazole weighed 195.4 g (1.17 moles). The liquid product mixture weighed 165.4 g and is composed of 70 percent 2-benzothiazyl-(3-triethoxysilyl)propyl disulfide and 15 percent bis(3-triethoxysilyl)propyl disulfide with the balance being mercaptobenzothiazole with a trace of 2,2'-dibenzothiazyl disulfide.

EXAMPLE 2

Preparation of 2-Benzothiazlyl-(3-Triethoxysilyl) Propyl Disulfide and Bis(3-Triethoxysilyl)Propyl Disulfide A 2-quart (1.89 l) glass reactor was charged with 1400 ml of chloroform, 142.8 g (0.60 mole) of 3-mercaptopropyltriethoxysilane, 216 g (0.60 mole) of 92 percent pure 2,2'-dibenzothiazyl disulfide with stirring. Within a few minutes, a mild exotherm to about 30° C. was noted and a clear amber solution formed. The reaction was stirred for 12 hours and a thick precipitate of mercaptobenzothiazole had formed and was removed by filtration. The chloroform was stripped under 29 inches of Hg vacuum, wherein the liquid product mixture was decanted from additional mercaptobenzothiazole. The combined dried mercaptobenzothiazole weighed 193.6 g (1.17 moles). The liquid product mixture weighed 161.3 g and was composed of 84 percent by weight 2-benzothiazyl-(3-triethoxysilyl) propyl disulfide and 5 percent by weight bis(3-triethoxysilyl)propyl disulfide with the balance being mercaptobenzothiazole with a trace of 2,2'-dibenzothiazyl disulfide.

EXAMPLE 3

Preparation of 2-Benzothiazyl-(3-Triethoxysilyl) Propyl Disulfide and Bis(3-Triethoxysilyl)Propyl Disulfide A reaction was carried out under the conditions of Example 1 except the 2-quart (1.89 l) glass reactor was charged with 1400 ml of chloroform, 284 g (1.193 moles of 3-mercaptopropyltriethoxysilane, 216 g (0.60 mole) of 92 percent pure 2,2'-dibenzothiazyl disulfide with stirring. Within several minutes, an exotherm to about 35° C. was noted and a solution formed. The reaction mixture was stirred for 24 hours and the precipitated mercaptobenzothiazole was filtered form the solution. The solvent was removed under reduced pressure at 29 inches of Hg vacuum, and the resulting liquid coupler mixture was decanted from additional mercaptobenzothiazole precipitate. The combined mercaptobenzothiazole precipitate was dried to give 198.6 g of material. The liquid product mixture weighed 236.5 g and was composed of 83 percent by weight of bis(3-triethoxysilyl)propyl disulfide and 13 percent by weight of 2-benzothiazyl-(3-triethoxysilyl)propyl disulfide as analyzed by GPC and mass spectrometric analysis.

EXAMPLE 4

Preparation of 2-Benzothiazyl-3-Triethoxysilyl) Propyl Disulfide and Bis(3-Triethoxysilyl)Propyl Disulfide A reaction was carried out under the conditions of Example 1 except the 2-quart (1.89 l) glass reactor was charged with 1400 ml of xylene, 284 g (1.193 moles) of 3-mercaptopropyltriethoxysilane, 216 g (0.60 mole) of 92 percent pure 2,2'-dibenzothiazyl disulfide with stirring. Within several minutes, an exotherm to about 35° C. was noted and a solution formed. The reaction mixture was stirred for 24 hours and the precipitated mercaptobenzothiazole was filtered from the solution. The solvent was removed under reduced pressure at 29 inches of Hg vacuum, and the resulting liquid mixture was decanted from additional mercaptobenzothiazole precipitate. The combined mercaptobenzothiazole precipitate was dried to give 196.8 g of material. The liquid product mixture weighed 230.5 g and was composed of 42 percent by weight of bis(3-triethoxysilyl)propyl disulfide and 56 percent by weight of 2-benzothiazyl-3-triethoxysilyl)propyl disulfide as analyzed by GPC and mass spectrometric analysis.

EXAMPLE 5

Preparation of 2-Benzothiazyl-3-Triethoxysilyl) Propyl Disulfide and Bis(3-Triethoxysilyl)Propyl Disulfide A 1-liter 3-neck round bottom flask was charged with 200 ml of mixed xylenes, 36 g (0.10 mole) of crude 2,2'-dibenzothiazyl disulfide, 23.8 g (0.10 mole) of 3-mercaptopropyltriethoxysilane, flushed with nitrogen and sealed under a nitrogen balloon. The reaction mixture was heated to reflux (145° C.) for 4 hours, cooled and filtered from long needles of mercaptobenzothiazole. The solvent was removed under a reduced pressure of 29 inches of Hg vacuum, and the liquid product, 18 g, was shown by GPC and mass spectrometric analysis to be 60 percent by weight of 2-benzothiazyl-3-triethoxysilyl) and 21 percent by weight of bis(3-triethoxysilyl)propyl disulfide with the remainder representing a mixture of mercaptobenzothiazole and 2,2'-dibenzothiazyl disulfide.

What is claimed is:

1. A process for the preparation of organosilicon disulfide compounds of the formula:

$$Z-R^1-S_2-R^1-Z \qquad \mathrm{I}$$

and

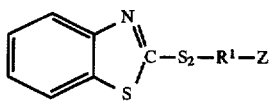

comprising reacting (a) a dithiobis(benzothiazole) compound of the formula

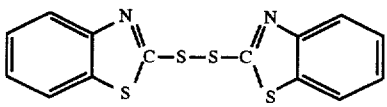

with (b) a mercaptosilane compound of the formula $$Z-R^1-SH \quad\quad IV$$

wherein Z is selected from the group consisting of

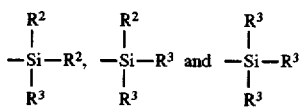

wherein $R^2$ may be the same or different and is independently selected from the group consisting of an alkyl group having 1 to 4 carbons and phenyl; $R^3$ may be the same or different and is independently selected from the group consisting of alkoxy groups having 1 to 8 carbon atoms and cycloalkoxy groups with 5 to 8 carbon atoms; and $R^1$ is selected from the group consisting of a substituted or unsubstituted alkylene group having a total of 1 to 18 carbon atoms and a substituted or unsubstituted arylene group having a total of 6 to 12 carbon atoms.

2. The process of claim 1 wherein

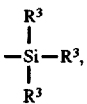

$R^3$ selected from the group consisting of alkoxy groups having 1 to 3 carbon atoms and $R^1$ is an alkylene group having 2 to 3 carbon atoms.

3. The process of claim 1 wherein the molar ratio of the compound of formula III to the compound of formula IV ranges from 1:5 to 5:1.

4. The process of claim 3 wherein the molar ratio of the compound of formula III to the compound of formula IV ranges from 1:3 to 3:1.

5. The process of claim 1 wherein said disulfide of formula I is selected from the group consisting of 2,2'-bis(trimethoxysilylethyl)disulfide; 3,3'-bis(trimethoxysilylpropyl)disulfide; 3,3'-bis(triethoxysilylpropyl)disulfide; 2,2'-bis(tripropoxysilylethyl)disulfide; 2,2'-bis(triethoxysilylpropyl)disulfide; 2,2'-bis(tri-sec-butoxysilylethyl)disulfide; 3,3'-bis(tri-t-butoxyethyl)disulfide; 3,3'-bis(triisopropoxysilylpropyl)disulfide; 3,3'-bis(trioctoxysilylpropyl)disulfide; 2,2'-bis(2'-ethylhexoxysilylethyl)disulfide; 2,2'-bis(dimethoxy ethoxysilylethyl)disulfide; 3,3'-bis(methoxyethoxypropoxysilylpropyl)disulfide; 3,3'-bis(dimethoxymethylsilylpropyl)disulfide; 3,3'-bis(methoxy dimethylsilylpropyl)disulfide; 3,3'-bis(diethoxymethylsilylpropyl)disulfide; 3,3'-bis(ethoxydimethylsilylpropyl)disulfide; 3,3'-bis(cyclohexoxy dimethylsilylpropyl)disulfide; 4,4'-bis(trimethoxysilylbutyl)disulfide; 3,3'-bis(trimethoxysilyl-3-methylpropyl)disulfide; 3,3'-bis(tripropoxysilyl-3-methylpropyl)disulfide; 3,3'-bis(dimethoxy methylsilyl-3-ethylpropyl)disulfide; 3,3'-bis(trimethoxysilyl-2-methylpropyl)disulfide; 3,3'-bis(dimethoxyphenylsilyl-2-methylpropyl)disulfide; 3,3'-bis(trimethoxysilylcyclohexyl)disulfide; 12,12'-bis(trimethoxysilyldodecyl)disulfide; 12,12'-bis(triethoxysilyldodecyl)disulfide; 18,18'-bis(trimethoxysilyloctadecyl)disulfide; 18,18'-bis(methoxydimethylsilyloctadecyl)disulfide; 2,2'-bis(trimethoxysilyl-2-methylethyl)disulfide; 2,2'-bis(tripropoxysilyl-2-methylethyl)disulfide; 2,2'-bis(trioctoxysilyl-2-methylethyl)disulfide; 2,2'-bis(trimethoxysilyl-phenyl)disulfide; 2,2'-bis(triethoxysilyl-phenyl)disulfide; 2,2'-bis(trimethoxysilyl-tolyl)disulfide; 2,2'-bis(triethoxysilyl-tolyl)disulfide; 2,2'-bis(trimethoxysilyl-methyl tolyl)disulfide; 2,2'-bis(triethoxysilyl-methyl tolyl)disulfide; 2,2'-bis(trimethoxysilyl-ethyl phenyl)disulfide; 2,2'-bis(triethoxysilyl-ethyl phenyl)disulfide; 2,2'-bis(trimethoxysilyl-ethyl tolyl)disulfide; 2,2'-bis(triethoxysilyl-ethyl tolyl)disulfide; 3,3'-bis(trimethoxysilyl-propyl phenyl) disulfide; 3,3'-bis(triethoxysilyl-propyl phenyl)disulfide; 3,3'-bis(trimethoxysilyl-propyl tolyl)disulfide; and 3,3'-bis(triethoxysilyl-propyl tolyl)disulfide.

6. The process of claim 1 wherein said disulfide of formula II is selected from the group consisting of 2-benzothiazyl-(3-triethoxysilylpropyl)disulfide; 2-benzothiazyl-(2-trimethoxysilylethyl)disulfide; 2-benzothiazyl-(3-trimethoxysilylpropyl)disulfide; 2-benzothiazyl-(2-triethoxysilylpropyl)disulfide; 2-benzothiazyl-(3-triethoxysilylpropyl)disulfide; 2-benzothiazyl-(2-tripropoxysilylethyl)disulfide; 2-benzothiazyl-(2-tri-sec-butoxysilylethyl)disulfide; 2-benzothiazyl-(3-tri-t-butoxysilylethyl)disulfide; 2-benzothiazyl-(3-triisopropoxysilylpropyl)disulfide; 2-benzothiazyl-(3-trioctoxysilylpropyl)disulfide; 2-benzothiazyl-(2-2'-ethylhexoxysilylethyl)disulfide; 2-benzothiazyl-(2-dimethoxy ethoxysilylethyl)disulfide; 2-benzothiazyl-(3-methoxyethoxypropoxysilylpropyl) disulfide; 2-benzothiazyl-(3-dimethoxymethylsilylpropyl) disulfide; 2-benzothiazyl-(3-methoxy dimethylsilylpropyl) disulfide; 3,3'-bis(diethoxymethylsilylpropyl)disulfide; 2-benzothiazyl-(3-diethoxymethylsilylpropyl)disulfide; 2-benzothiazyl-(3-ethoxydimethylsilylpropyl)disulfide; 2-benzothiazyl-(3-cyclohexoxy dimethylsilylpropyl) disulfide; 2-benzothiazyl-(4-trimethoxysilylbutyl)disulfide; 2-benzothiazyl-(3-trimethoxysilyl-3-methylpropyl) disulfide; 2-benzothiazyl-(3-tripropoxysilyl-3-methylpropyl)disulfide; 2-benzothiazyl-(3-dimethoxy methylsilyl-3-ethylpropyl)disulfide; 2-benzothiazyl-(3-trimethoxysilyl-2-methylpropyl)disulfide; 2-benzothiazyl-(3-dimethoxyphenylsilyl-2-methylpropyl)disulfide; 2-benzothiazyl-(3-trimethoxysilylcyclohexyl)disulfide; 2-benzothiazyl-(12-trimethoxysilyldodecyl)disulfide; 2-benzothiazyl-(12-triethoxysilyldodecyl)disulfide; 2-benzothiazyl-(18-trimethoxysilyloctadecyl)disulfide; 2-benzothiazyl-(18omethoxydimethylsilyloctadecyl) disulfide; 2-benzothiazyl-(2-trimethoxysilyl-2-methylethyl) disulfide; 2-benzothiazyl-(2-tripropoxysilyl-2-methylethyl) disulfide; 2-benzothiazyl-(2-trioctoxysilyl-2-methylethyl) disulfide; 2-benzothiazyl-(2-trimethoxysilyl-phenyl) disulfide; 2-benzothiazyl-(2-triethoxysilyl-phenyl)disulfide; 2-benzothiazyl-(2-trimethoxysilyltolyl)disulfide; 2-benzothiazyl-(2-triethoxysilyltolyl)disulfide;

2-benzothiazyl-(2-trimethoxysilylmethyl tolyl)disulfide;
2-benzothiazyl-(2-triethoxysilyl-methyl tolyl)disulfide;
2-benzothiazyl-(2-trimethoxysilyl-ethyl phenyl)disulfide;
2-benzothiazyl-(2-triethoxysilyl-ethyl phenyl)disulfide;
2-benzothiazyl-(2-trimethoxysilylethyl tolyl)disulfide;
2-benzothiazyl-(2-triethoxysilyl-ethyl tolyl)disulfide;
2-benzothiazyl-(3-trimethoxysilyl-propyl phenyl)disulfide;
2-benzothiazyl-(3-triethoxysilyl-propyl phenyl)disulfide;
2-benzothiazyl-(3-trimethoxysilyl-propyl tolyl)disulfide;
and 2-benzothiazyl-(3-triethoxysilyl-propyl tolyl)disulfide.

7. The process of claim 1 wherein said mercaptosilane compound of formula IV is selected from a group consisting of 2-mercaptoethyl trimethoxysilane, 3-mercaptopropyl trimethoxysilane, 2-mercaptopropyl triethoxysilane, 3-mercaptopropyl triethoxysilane, 2-mercaptoethyl tripropoxysilane, 2-mercaptoethyl tri sec-butoxysilane, 3-mercaptopropyl tri-t-butoxysilane, 3-mercaptopropyl tri-isopropoxysilane; 3-mercaptopropyl trioctoxysilane, 2-mercaptoethyl tri-2'-ethylhexoxysilane, 2-mercaptoethyl dimethoxy ethoxysilane, 3-mercaptopropyl methoxyethoxypropoxysilane, 3-mercaptopropyl dimethoxy methylsilane, 3-mercaptopropyl methoxy dimethylsilane, 3-mercaptopropyl ethoxy dimethylsilane, 3-mercaptopropyl diethoxy methylsilane, 3-mercaptopropyl cyclohexoxy dimethyl silane, 4-mercaptobutyl trimethoxysilane, 3-mercapto-3-methylpropyltrimethoxysilane, 3-mercapto-3-methylpropyl-tripropoxysilane, 3-mercapto-3-ethylpropyl-dimethoxy methylsilane, 3-mercapto-2-methylpropyl trimethoxysilane, 3-mercapto-2-methylpropyl dimethoxy phenylsilane, 3-mercaptocyclohexyl-trimethoxysilane, 12-mercaptododecyl trimethoxy silane, 12-mercaptododecyl triethoxy silane, 18-mercaptooctadecyl trimethoxysilane, 18-mercaptooctadecyl methoxydimethylsilane, 2-mercapto-2-methylethyltripropoxysilane, 2-mercapto-2-methylethyltrioctoxysilane, 2-mercaptophenyl trimethoxysilane, 2-mercaptophenyl triethoxysilane; 2-mercaptotolyl trimethoxysilane; 2-mercaptotolyl triethoxysilane; 1-mercaptomethyltolyl trimethoxysilane; 1-mercaptomethyltolyl triethoxysilane; 2-mercaptoethylphenyl trimethoxysilane; 2-mercaptoethylphenyl triethoxysilane; 2-mercaptoethyltolyl trimethoxysilane; 2-mercaptoethyltolyl triethoxysilane; 3-mercaptopropylphenyl trimethoxysilane; 3-mercaptopropylphenyl triethoxysilane; 3-mercaptopropyltolyl trimethoxysilane; and 3-mercaptopropyltolyl triethoxysilane.

8. The process of claim 1 wherein said reaction is in absence of water and in the presence of an organic solvent selected from the group consisting of chloroform, dichloromethane, carbon tetrachloride, hexane, heptane, cyclohexane, xylene, benzene, dichloroethylene, trichloroethylene, dioxane, diisopropyl ether, tetrahydrofuran and toluene.

9. The process of claim 1 wherein the reaction is conducted at a temperature ranging from 20° C. to 140° C.

10. The process of claim 9 wherein the reaction is conducted at a temperature ranging from 50° C. to 90° C.

11. The process of claim 1 wherein the reaction is conducted at a pressure ranging from 0.096 to 4.83 kg/cm$^2$.

* * * * *

UNITED STATES PATENT AND TRADEMARK OFFICE
CERTIFICATE OF CORRECTION

PATENT NO. : 5,675,014
DATED : October 7, 1997
INVENTOR(S) : Cohen et al

It is certified that error appears in the above-indentified patent and that said Letters Patent is hereby corrected as shown below:

Delete Formula III in Column 2, lines 3-7,

"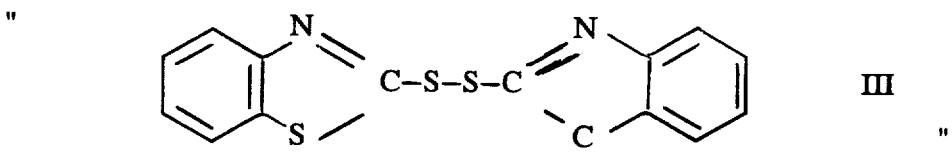 III "

and substitute therefor with

--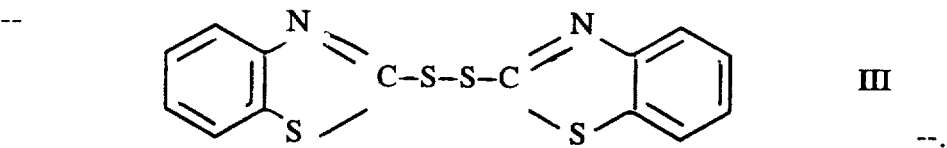 III --.

Signed and Sealed this

Seventh Day of April, 1998

Attest:

Attesting Officer

BRUCE LEHMAN

Commissioner of Patents and Trademarks